US011116939B2

(12) United States Patent
Jamous et al.

(10) Patent No.: US 11,116,939 B2
(45) Date of Patent: Sep. 14, 2021

(54) RAPID EXCHANGE BALLOON CATHETER

(71) Applicant: Medtronic Vascular, Inc., Santa Rosa, CA (US)

(72) Inventors: Aram Jamous, Galway (IE); David Gannon, Galway (IE); James Hannon, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 133 days.

(21) Appl. No.: 16/292,977

(22) Filed: Mar. 5, 2019

(65) Prior Publication Data

US 2019/0275295 A1    Sep. 12, 2019

Related U.S. Application Data

(60) Provisional application No. 62/639,213, filed on Mar. 6, 2018.

(51) Int. Cl.
*A61M 25/01* (2006.01)
*A61F 2/958* (2013.01)
(Continued)

(52) U.S. Cl.
CPC .............. *A61M 25/01* (2013.01); *A61F 2/958* (2013.01); *A61L 29/02* (2013.01);
(Continued)

(58) Field of Classification Search
CPC ...... A61M 2025/0183; A61M 25/0052; A61M 25/01; A61M 25/09; A61M 25/0043;
(Continued)

(56) References Cited

U.S. PATENT DOCUMENTS

| 4,545,390 A | 10/1985 | Leary |
| 5,205,830 A | 4/1993 | Dassa et al. |

(Continued)

FOREIGN PATENT DOCUMENTS

| EP | 1787673 A1 | 5/2007 |
| EP | 2829299 A1 | 1/2015 |

(Continued)

OTHER PUBLICATIONS

PCT/US2019/020715, The International Search Report and the Written Opinion of the International Searching Authority, dated Jun. 6, 2019, 16pgs.

*Primary Examiner* — Jocelin C Tanner
(74) *Attorney, Agent, or Firm* — Dicke, Billig & Czaja, PLLC (57) ABSTRACT

A balloon catheter including a catheter shaft, a balloon and a support assembly. The catheter shaft defines an internal shoulder and carries the balloon. The support assembly includes a first member and a second member. The second member defines opposing, leading and trailing ends, and is arranged over the first member such that the leading end is distal the trailing end. The leading end is free of direct physical attachment to the first member. The support assembly extends within a lumen of the catheter shaft and the leading end bears against the internal shoulder. A pushing force applied at a proximal region of the catheter shaft is transferred onto the internal shoulder via the support assembly. The support assembly is simple and inexpensive. Further, the leading end of the second member is transversely moveable relative to the first member, thereby minimizing possible kinking of the first member.

18 Claims, 10 Drawing Sheets

(51) Int. Cl.
*A61M 25/10* (2013.01)
*A61L 29/02* (2006.01)
*A61M 25/00* (2006.01)
*A61M 25/09* (2006.01)

(52) U.S. Cl.
CPC .... *A61M 25/0032* (2013.01); *A61M 25/0052* (2013.01); *A61M 25/104* (2013.01); *A61M 25/1034* (2013.01); *A61M 25/1036* (2013.01); *A61M 25/09* (2013.01); *A61M 2025/0177* (2013.01); *A61M 2025/0183* (2013.01); *A61M 2025/1061* (2013.01)

(58) Field of Classification Search
CPC ........ A61M 25/104; A61M 2025/0059; A61M 2025/0063; A61M 25/1034; A61M 25/0032; A61M 25/1036; A61M 25/0102; A61M 25/0071; A61M 2025/0177; A61M 2025/1061; A61M 2025/1056; A61F 2/958; A61F 2002/9583; A61F 2002/9586; A61F 2/2433; A61L 29/02
See application file for complete search history.

(56) References Cited

U.S. PATENT DOCUMENTS

| | | | |
|---|---|---|---|
| 5,290,306 A | 3/1994 | Trotta et al. | |
| 5,318,529 A | 6/1994 | Kontos | |
| 5,429,597 A | 7/1995 | DeMello et al. | |
| 5,441,484 A | 8/1995 | Atkinson et al. | |
| 5,490,837 A * | 2/1996 | Blaeser | A61M 25/104 604/103.11 |
| 5,800,391 A | 9/1998 | Kontos | |
| 5,810,867 A | 11/1998 | Zarbatany et al. | |
| 6,042,589 A * | 3/2000 | Marianne | A61F 2/95 606/108 |
| 6,066,114 A * | 5/2000 | Goodin | A61M 25/104 604/103.04 |
| 6,210,346 B1 | 4/2001 | Hall et al. | |
| 6,368,302 B1 | 4/2002 | Fitzmaurice et al. | |
| 6,475,187 B1 | 11/2002 | Gerberding | |
| 6,706,055 B2 | 3/2004 | Douk et al. | |
| 7,762,984 B2 | 7/2010 | Kumoyama et al. | |
| 8,864,705 B2 | 10/2014 | Nishigishi | |
| 2002/0177841 A1 | 11/2002 | Moloney et al. | |
| 2006/0282110 A1 | 12/2006 | Litvack et al. | |
| 2007/0005041 A1* | 1/2007 | Frassica | A61B 1/0008 604/544 |
| 2007/0083188 A1 | 4/2007 | Grandt et al. | |
| 2010/0217234 A1 | 8/2010 | Grovender et al. | |
| 2012/0226231 A1* | 9/2012 | Nishigishi | A61M 25/0102 604/103.09 |
| 2012/0296367 A1 | 11/2012 | Grovender et al. | |
| 2012/0303054 A1* | 11/2012 | Wilson | A61M 25/0052 606/194 |
| 2013/0197432 A1* | 8/2013 | Von Oepen | A61F 2/958 604/96.01 |
| 2014/0171736 A1* | 6/2014 | Stigall | A61B 5/0084 600/109 |
| 2014/0379065 A1* | 12/2014 | Johnson | A61F 2/97 623/1.11 |
| 2015/0005803 A1* | 1/2015 | Erikawa | A61M 25/0052 606/194 |
| 2015/0246203 A1* | 9/2015 | Ciurea | B29C 57/04 156/293 |
| 2018/0078743 A1* | 3/2018 | Kubo | A61M 25/10 |
| 2018/0296233 A1* | 10/2018 | Schwager | A61B 17/22 |

FOREIGN PATENT DOCUMENTS

| | | |
|---|---|---|
| EP | 2709706 B1 | 6/2015 |
| WO | 9318816 A1 | 11/1993 |
| WO | 2011011765 A2 | 1/2011 |

\* cited by examiner

RAPID EXCHANGE BALLOON CATHETER

CROSS-REFERENCE TO RELATED APPLICATIONS

This Non-Provisional patent application claims the benefit of the filing date of U.S. Provisional Patent Application Ser. No. 62/639,213, filed Mar. 6, 2018, the entire teachings of which are incorporated herein by reference.

BACKGROUND

The present disclosure relates to balloon catheters. More particularly, it relates to rapid exchange balloon catheters.

Balloon catheters are inserted into various locations within a patient for a wide variety of purposes and medical procedures. For example, techniques for treating stenosis or occlusion of a blood vessel include balloon angioplasty in which a balloon catheter is inserted into the narrowed or blocked area, and the balloon is inflated to expand the constricted area. Balloon catheters are also commonly used to deliver and deploy a stent or other medical device at an internal target site of the patient's anatomy. Regardless, balloon catheter insertion typically requires the use of a guidewire, particularly where the balloon catheter carries a stent or other relatively bulky therapeutic device. The guidewire may be inserted into a patient's vasculature through the skin, and advanced to (and possibly beyond) the treatment location. Alternatively, the guidewire and the balloon catheter may be advanced together, with the guidewire protruding from a distal end of the balloon catheter.

There are various types of balloon catheters, one of which is a "rapid exchange" or single operator balloon catheter. A rapid exchange balloon catheter includes an outer catheter shaft (e.g., a single catheter, tube, sheath, etc., or a combination of catheter(s), tube(s), sheath(s), etc., assembled to one another) maintaining the balloon, along with a short tube defining a guidewire lumen open to a distal end or tip of the balloon catheter. The tube extends proximally through the balloon and is open to an exterior of the outer catheter shaft at a guidewire port (or other opening such as a slit) located proximal a proximal end of the balloon. The guidewire tube is isolated from an inflation lumen(s) of the outer catheter shaft through which an inflation medium is delivered from a proximal region of the balloon catheter to an interior of the balloon. With this construction, most of the length of the guidewire extends exteriorly of the balloon catheter. The balloon catheter can be removed or exchanged for another rapid exchange catheter without the need for a relatively long guidewire (a concern or disadvantage of "over-the-wire" catheter systems).

To address possible pushability and/or column strength concerns, some rapid exchange balloon catheter designs incorporate an internal wire (e.g., push wire, stiffening wire, core wire, etc.). The internal wire can be connected to a proximal region of the outer catheter shaft, extending within the outer catheter shaft to increase an overall stiffness of the balloon catheter. With these and similar constructions, the internal wire can enhance the transmission of a pushing force applied by the user at a proximal end of the balloon catheter to the distal end. In this regard, the rapid exchange balloon catheter can be designed such that a distal region of the internal wire directly contacts an interior surface of the outer catheter shaft; with this arrangement, a pushing force applied to the internal wire is more directly transmitted to the region of the outer catheter shaft otherwise in contact with the internal wire, for example at or near the guidewire port (or rapid exchange joint).

While highly viable, construction and assembly of the internal wire and corresponding outer catheter shaft as part of a rapid exchange balloon catheter can be complex and expensive. So as to not overtly obstruct or limit the size of the inflation lumen(s) of the outer catheter shaft, the internal wire is typically thin and can have a tapering distal end. It can be difficult and costly to machine or grind the spatial features into a thin wire that are otherwise necessary for desired interface/contact with the outer catheter shaft. Along these same lines, the interior contact surface(s) of the outer catheter shaft may be complex and thus more difficult to generate. Moreover, an anchored relationship between the internal wire and the outer catheter shaft may undesirably promote kink formation in the internal wire when traversing a tortuous pathway.

SUMMARY

The inventors of the present disclosure recognized that a need exists for a balloon catheter that address one or more of the above-mentioned problems.

Some aspects of the present disclosure relate to a balloon catheter including a catheter shaft, a balloon and a support assembly. The catheter shaft defines a plurality of lumens and an internal shoulder. The balloon is carried by the catheter shaft, and an interior of the balloon is fluidly open to at least one of the plurality of lumens. The support assembly includes a first member and a second member. The first member extends between opposing, proximal and distal ends. The second member is disposed over the first member and defines opposing, leading and trailing ends. In this regard, the second member is arranged such that the leading end is distal the trailing end. Further, the leading end of the second member is free of direct physical attachment to the first member. Finally, the support assembly extends within one of the plurality of lumens and the leading end of the second member bears against the internal shoulder. With this construction, a pushing force applied at a proximal region of the catheter shaft is transferred onto the internal shoulder via the support assembly. The support assembly is simple and inexpensive. Further, the leading end of the second member is transversely moveable relative to the first member, thereby minimizing possible kinking of the first member as the balloon catheter is caused to traverse a tortuous pathway.

Other aspects of the present disclosure are directed toward a method of manufacturing a balloon catheter. The method includes forming a support assembly. The step of forming the support assembly includes providing a first member, and providing a second member apart from the first member. The first member extends between opposing, proximal and distal ends. The second member defines opposing, leading and trailing ends. The second member is disposed over the first member such that leading end is distal the trailing end. Further, the leading end is free of direct physical attachment to the first member. A catheter shaft is provided including a proximal shaft segment and a distal shaft segment. The support assembly is assembled to the catheter shaft such that the first member is attached to the proximal shaft segment and the leading end bears against an internal shoulder of the distal shaft segment. A balloon is assembled onto the catheter shaft, including an interior of the balloon in fluid communication with an inflation lumen of the catheter shaft. In some embodiments, the step of forming the support assembly includes physically attaching the trailing end of the second member to the first member; in other embodiments, an entirety of the second member is free of direct physical attachment to the first member. Regardless, the support assembly is simply and inexpensively formed.

Yet other aspects of the present disclosure are directed to methods of performing a surgical procedure on a patient. The method includes directed a guidewire to a target site within the patient. A balloon catheter is advanced over the guidewire. The balloon catheter includes a catheter shaft, a balloon and a support assembly. The catheter shaft defines a plurality of lumens and an internal shoulder. The balloon is carried by the catheter shaft, and an interior of the balloon is fluidly open to at least one of the plurality of lumens. The support assembly includes a first member and a second member. The first member extends between opposing, proximal and distal ends. The second member is disposed over the first member and defines opposing, leading and trailing ends. In this regard, the second member is arranged such that the leading end is distal the trailing end. Further, the leading end of the second member is free of direct physical attachment to the first member. Finally, the support assembly extends within one of the plurality of lumens and the leading end of the second member bears against the internal shoulder. The step of advancing includes the support assembly transferring a pushing force applied to a proximal region of the catheter shaft onto a region of the catheter shaft distal the proximal region. The balloon is then inflated and later deflated. The balloon catheter is withdrawn from the patient. The surgical procedure can be or include angioplasty, delivery of a stent or stented device, and the like.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein with reference to an implanted medical device such as a stent or stented valve prosthesis, the terms "distal", "outlet", and "outflow" are understood to mean downstream to the direction of blood flow, and the terms "proximal", "inlet", or "inflow" are understood to mean upstream to the direction of blood flow. In addition, as used herein, the terms "outward" or "outwardly" refer to a position radially away from a longitudinal axis of the balloon catheter or the longitudinal axis of a stent or frame of an implanted medical device such a frame of a valve prosthesis and the terms "inward" or "inwardly" refer to a position radially toward a longitudinal axis of the balloon catheter or the stent or fame of an implanted medical device such as the frame of the valve prosthesis. As well the terms "backward" or "backwardly" refer to the relative transition from a downstream position to an upstream position and the terms "forward" or "forwardly" refer to the relative transition from an upstream position to a downstream position.

Figure 1:
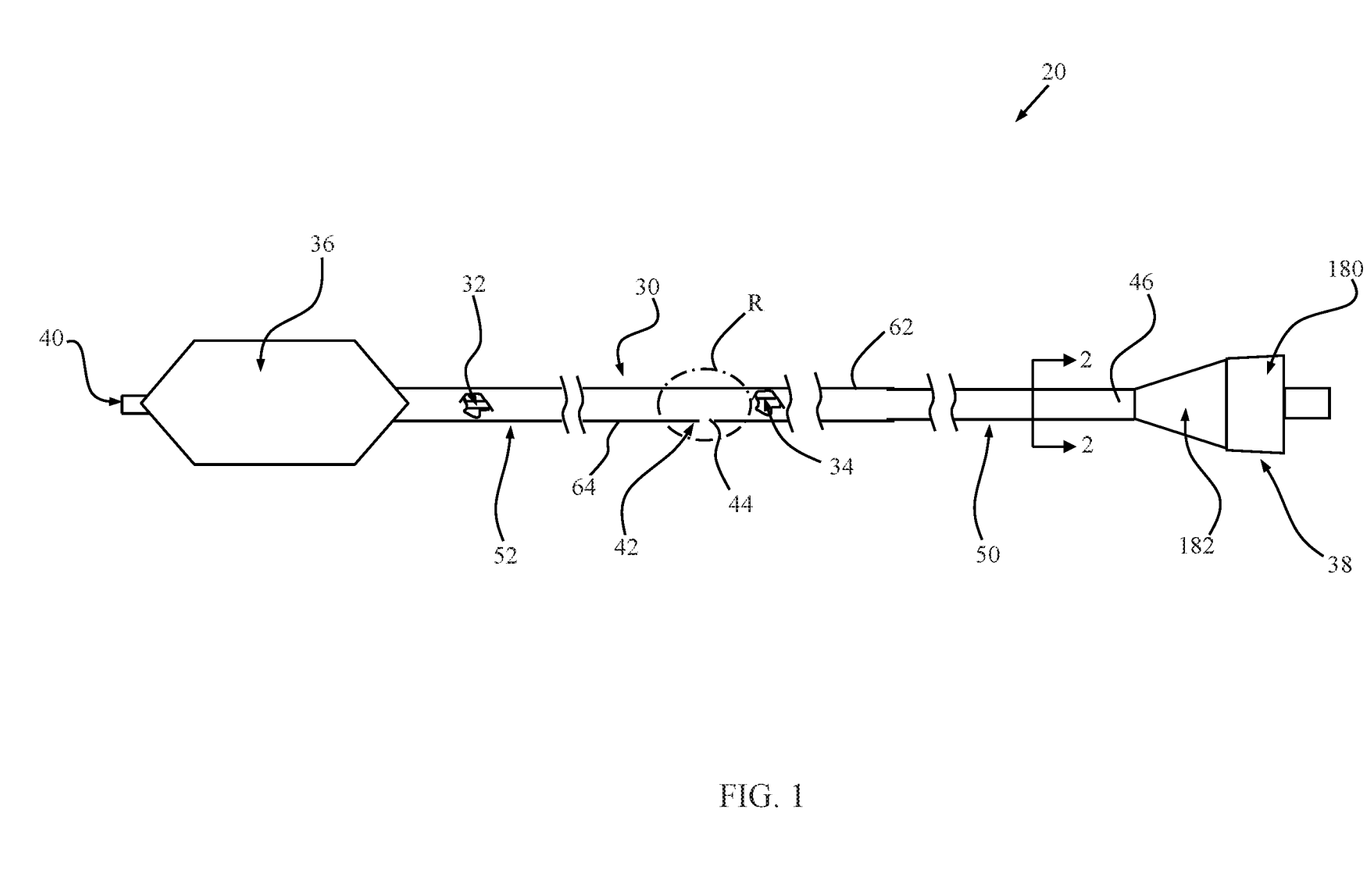
FIG. 1 is a simplified side view of a balloon catheter in accordance with principles of the present disclosure.

An exemplary balloon catheter 20 in accordance with principles of the present disclosure is shown in simplified form in FIG. 1. The balloon catheter 20 includes a catheter shaft 30, a guidewire tube (or inner shaft) 32, a support assembly 34 (referenced generally), a balloon 36 and a hub assembly 38. Details on the various components are provided below. In general terms, however, the catheter shaft 30 carries the balloon 36 adjacent a distal end 40 thereof, and forms one or more inflation lumens (hidden) in fluidly communication with an interior of the balloon 36. Further, the balloon catheter 20 defines a rapid exchange joint 42 (referenced generally) including a guidewire port 44 that is otherwise open to an exterior of the catheter shaft 30. The guidewire tube 32 is fluidly open to the guidewire port 44, and extends distally from the rapid exchange joint 42 within the catheter shaft 30 and through the balloon 36. The support assembly 34 extends within the catheter shaft 30, and interfaces with internal features of the catheter shaft 30 as described below. The hub assembly 38 is connected to a proximal end 46 (referenced generally) of the catheter shaft 30, and provides access to the inflation lumen(s). With this construction, the balloon catheter 20 incorporates rapid exchange features whereby a guidewire (not shown) is slidably engaged via the rapid exchange joint 42 and the guidewire tube 32. The support assembly 34 interfaces with interior features of the catheter shaft 30 (e.g., in a region of the rapid exchange joint 42), serving to transfer a pushing force applied in a region of the proximal end 46. In this regard, features of the support assembly 34 intended to interact with the catheter shaft 30 are readily generated on a cost-effective basis, and optionally promote independent radial or lateral movement relative to the catheter shaft 30.

Figure 2:
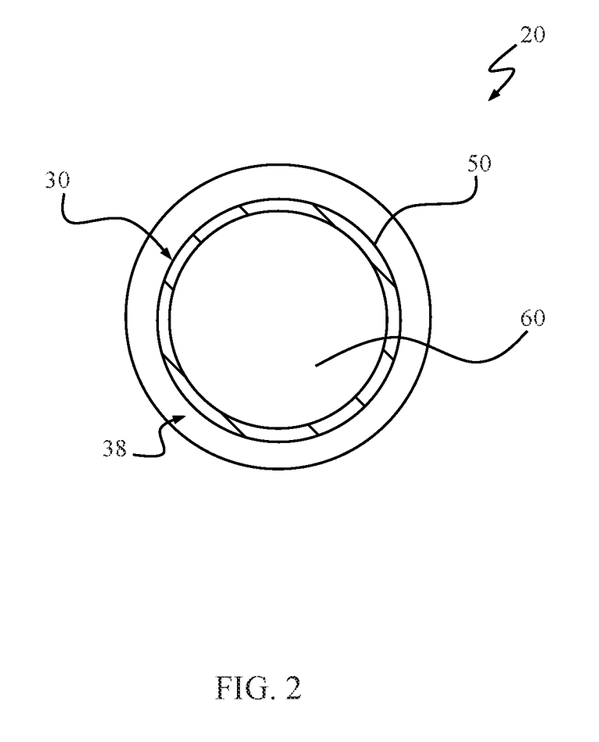
FIG. 2 is a cross-section view of the balloon catheter of FIG. 1, taken along the line 2-2.

The catheter shaft 30 can assume various forms, and in some embodiments can include two or more separately formed and subsequently assembled components. For example, in the non-limiting embodiment of FIG. 1, the catheter shaft 30 includes or is formed by a proximal shaft segment 50 and a distal shaft segment 52. In general terms, the shaft segments 50, 52 can each be generally tubular bodies, with the proximal shaft segment 50 having an elevated stiffness as compared to the distal shaft segment 52. For example, the proximal shaft segment 50 can be, or can include, a metal tube (e.g., a hypotube), whereas the distal shaft segment 52 can be, or can be akin to, a conventional catheter or sheath. With embodiments in which the proximal shaft segment 50 is or includes a hypotube, various, surgically-safe constructions can be employed. Thus, the proximal segment 50 can be or include a stainless steel hypotube, such as 304L stainless steel. Optionally, various coatings can be applied to the metal hypotube, such as Teflon® paint or coating. Regardless, and as reflected by FIG. 2, the proximal shaft segment 50 defines at least one lumen, such as proximal shaft segment lumen 60.

Returning to FIG. 1, the distal shaft segment 52 can be can be a flexible, polymeric tubular body akin to a conventional catheter. In some embodiments, the distal shaft segment 52 can include or comprise two or more components, such as a transition portion 62 and a distal portion 64. With these and similar embodiments, the transition portion 62 is bonded to or otherwise secured over an exterior of the proximal shaft segment 50 as generally reflected by FIG. 1 (e.g., the transition portion 62 can be a sleeve made from a heat shrink material), and serves as a transition to the distal portion 64. The rapid exchange joint 42, in turn, can be formed by a combination of the guidewire tube 34, and the transition and distal portions 62, 64 (e.g., using conventional catheter manufacturing techniques, the guidewire tube 32, the transition portion 62 and the distal portion 64 can be melted together and combined in forming the completed distal shaft segment 52 and rapid exchange joint 42). Alternatively, the distal shaft segment 52 can be formed by four or more components, two components, or as a single homogenous body.

Figure 3:
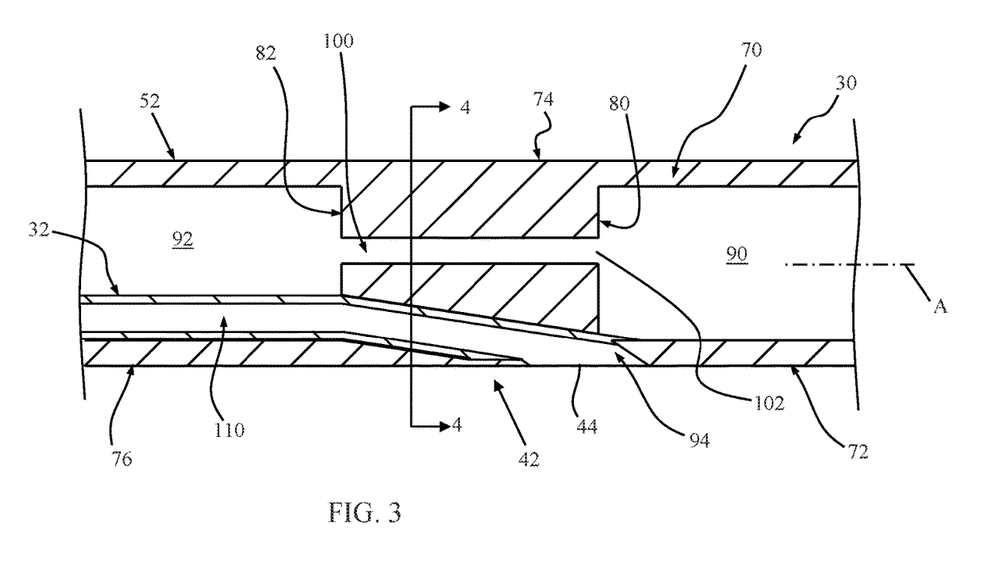
FIG. 3 is an enlarged cross-sectional view of a region of the balloon catheter of FIG. 1 with portions removed.

With the above in mind, a portion of the catheter shaft 30 and the guidewire tube 32 are shown in isolation in FIG. 3 (i.e., the support assembly 34 (FIG. 1) is omitted from the view of FIG. 3 for ease of understanding), and in particular a longitudinal cross-section of the catheter shaft 30 and the guidewire tube 32 at the region R identified in FIG. 1. With the non-limiting construction of FIG. 3, the distal shaft segment 52 of the catheter shaft 30 includes a tubular sidewall 70 defining a first region 72, a second region 74, and a third region 76. The second region 74 is intermediate the first and third regions 72, 76 (with the third region 76 being distal the first region 72), and a wall thickness of the tubular sidewall 70 is increased at the second region 74 (as compared to a wall thickness along the first and third regions 72, 76) in generating the rapid exchange joint 42. Stated otherwise, the tubular sidewall 70 defines a central longitudinal axis A. Opposing, proximal and distal internal shoulders 80, 82 are defined along the second region 74 as radially inward (relative to the central longitudinal axis A) projections. One or both of the proximal and distal internal shoulders 80, 82 can optionally be characterized as being substantially planar surface (i.e., within 10% of a truly planar surface) and substantially perpendicular (i.e., within 10 degrees of a truly perpendicular relationship) to the central longitudinal axis A. While the second region 74, and in particular the proximal and distal internal shoulders 80, 82, is illustrated in FIG. 3 as being integrally formed by the tubular sidewall 70 as a homogenous body (e.g., a wall thickness of the tubular sidewall 70 is increased along the second region 74 to define the internal shoulders 80, 82), other constructions are also acceptable. For example, the tubular sidewall 70 can have a more uniform wall thickness, and the internal shoulders 80, 82 can be provided by a body (or bodies) formed apart from and internally mounted to the tubular sidewall 70.

The rapid exchange joint 42 further includes one or more passages or lumens formed through a thickness of the tubular sidewall 70 and open to the distal internal shoulder 82. As a point of reference, the tubular sidewall 70 defines a primary lumen, with the increased thickness along the second region 74 projecting into, or decreasing a size of, the primary lumen. Thus, the distal shaft segment 52 can be viewed as including or defining an upstream primary lumen 90 that extends proximally from the proximal internal shoulder 80, and a downstream primary lumen 92 that extends distally from the distal internal shoulder 82. The upstream primary lumen 90 is in fluid communication with the proximal shaft segment lumen 60 (FIG. 2) of the proximal shaft segment 50 (FIG. 1); the downstream primary lumen 92 is in fluid communication with an interior of the balloon 36 (FIG. 1). With this mind, the rapid exchange joint 42 includes the guidewire port 44 being defined at or through an exterior of the tubular sidewall 70 along the second region 74 at a location longitudinally between the proximal and distal shoulders 80, 82. A guidewire passageway 94 extends from the guidewire port 44 and through the tubular sidewall 70. In some embodiments, the guidewire passageway 94 is generated by forming, molding or melting the catheter shaft 30 about the guidewire tube 32 as described below, about a mandrel, etc. With these and similar constructions, the guidewire passageway 94 can extend to the distal internal shoulder 82 (it being understood that the guidewire tube 32 is disposed within the guidewire passageway, and extends distally from the distal internal shoulder 82. In more general terms, the guidewire passageway 94 locates the guidewire tube 32 for passage of a guidewire (not shown) from an exterior of the tubular sidewall 70 to an interior of the tubular sidewall 70.

FIG. 3 further illustrates that in some embodiments, one or more additional lumens can be defined by the catheter shaft 30 at the rapid exchange joint 42, such as a transition lumen 100. The transition lumen 100 is open to (i.e., in fluid communication with) the upstream primary lumen 90 at the proximal internal shoulder 80 via an opening 102. In some embodiments, the transition lumen 100 can further be open to (i.e., in fluid communication with) the downstream primary lumen 92 at the distal internal shoulder 82; in other embodiments, the transition lumen 100 can terminate proximal the distal internal shoulder 82 and is closed (i.e., not in fluid communication with) relative to the downstream primary lumen 92. Regardless, the transition lumen 100, including the opening 102, is sized and shaped to slidably receive a portion of the support assembly 34 (FIG. 1), as well as to promote desired interface between the support assembly 34 and the proximal internal shoulder 80 as described in greater detail below.

Figure 4:
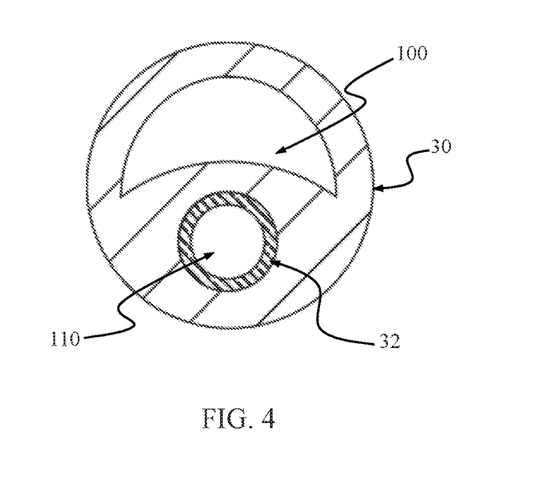
FIG. 4 is a cross-sectional view of the balloon catheter of FIG. 3, taken along the line 4-4.

With embodiments in which the transition lumen 100 is open to both upstream and downstream primary lumens 90, 92, the upstream and downstream primary lumens 90, 92 are fluidly connected to one another by the first transition lumen 100. With this non-limiting construction, an inflation medium supplied to the upstream primary lumen 90 can be delivered to the downstream primary lumen 92 (and thus the balloon 36 (FIG. 1)) via the transition lumen 100. In other words, the upstream primary lumen 90, the transition lumen 100, and the downstream primary lumen 92 can collectively define an inflation lumen of the distal shaft segment 52 and through which an inflation medium is delivered to and from the balloon 36. Thus, and as shown in FIG. 4, the transition lumen 100 can be sized and shaped (e.g., C-shaped) to interface with the support assembly 34 (FIG. 1) as described below and to permit passage of the inflation medium.

Alternatively, two (or more) additional transition lumens can be provided at the rapid exchange joint 42 that further facilitate passage of an inflation medium. Under circumstances where fluid flow through the transition lumen 100 is obstructed (e.g., by a portion of the support assembly 34 (FIG. 1) as described below), requisite inflation medium flow can occur primarily through the additional transition lumen(s).

Returning to FIG. 1, the rapid exchange joint 42 can be formed in a wide variety of other manners that may or may not be implicated by the descriptions above. Moreover, the catheter shaft 30 can assume a wide variety of other forms, and is not limited to the shaft segment constructions described above. In more general terms, any rapid exchange balloon catheter configuration including at least one internal shoulder (e.g., the proximal internal shoulder 80 (FIG. 3)) and a transition lumen open to the internal shoulder (e.g., the transition lumen 100 (FIG. 3)) is acceptable.

The guidewire tube 32 can assume various forms conducive to slidably receiving a medical guidewire (not shown), and defines a guidewire lumen 110. To provide free-sliding movement over a medical guidewire, the guidewire tube 32 can be fabricated from flexible low-friction polymers such as polytetrafluoroethylene (PTFE) or polyolefin. Alternatively, the guidewire tube 32 can be made from a polymer selected without regard to its friction properties, and a slippery coating can be applied to the guidewire lumen 110 to reduce friction along the guidewire. Regardless, the guidewire tube 32 is mounted to the catheter shaft 30 such that the guidewire lumen 110 is in fluid communication with the guidewire port 44. For example, the guidewire tube 32 can be melted to or otherwise formed with components of the catheter shaft 30 in forming the rapid exchange joint 42. Alternatively, a proximal side of the guidewire tube 32 can be bonded or otherwise adhered to the distal internal shoulder 82; can be bonded or press-fit into the guidewire passageway 94; etc. As shown, the guidewire tube 32 is maintained within the downstream primary lumen 92, extending distally from the distal internal shoulder 82. With additional reference to FIG. 1, the guidewire tube 32 terminates at a distal side (hidden) that is open to an opening at the distal end 40 of the catheter shaft 30. Other constructions establishing a guidewire lumen extending between (and open to) the distal end 40 and the guidewire port 44 appropriate for slidably receiving a guidewire are equally acceptable, and may or may not include the guidewire tube 32.

Figure 5:
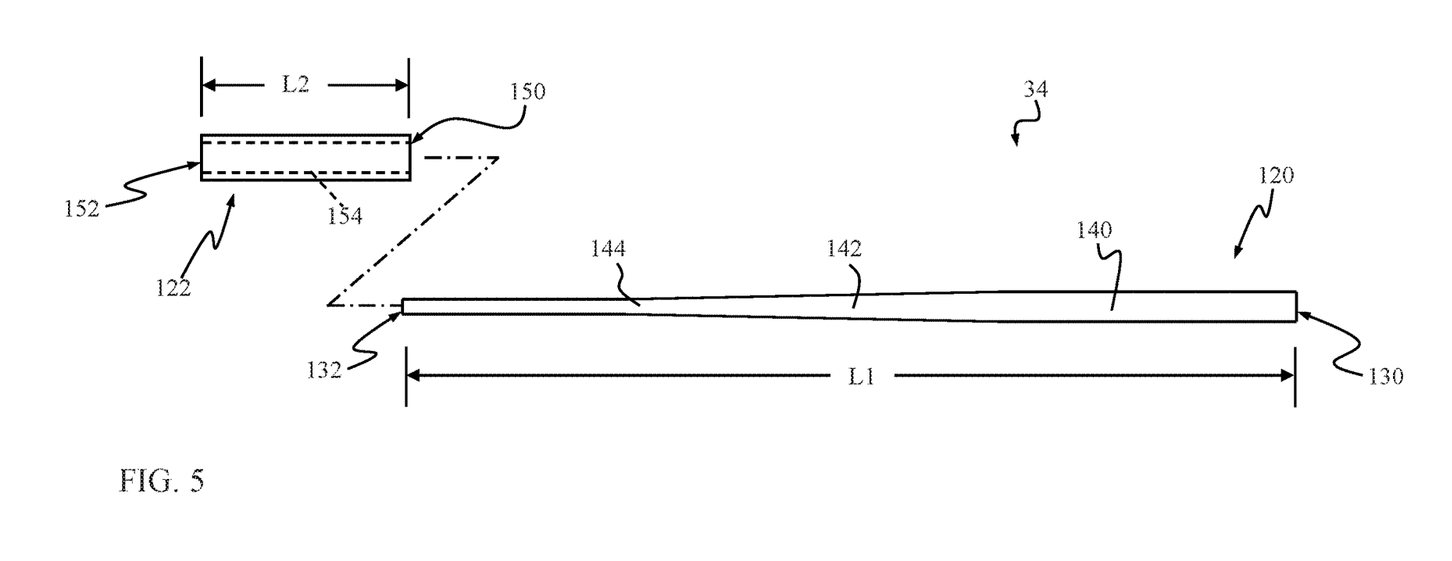
FIG. 5 is a simplified, exploded side view of a support assembly in accordance with principles of the present disclosure and useful with the balloon catheter of FIG. 1.

One embodiment of the support assembly 34 is shown in simplified form in FIG. 5. The support assembly 34 includes a first member 120 and a second member 122. In general terms, the first member 120 is configured for assembly to other component(s) of the balloon catheter 20 (FIG. 1) as described in greater detail below. The second member 122 is configured to be received over the first member 120, and provides a bearing surface for reasons made clear below.

The first member 120 has an elongated shape defining opposing, proximal and distal ends 130, 132, and a longitudinal length L1. In some embodiments, a shape or profile of the first member 120 can vary between the proximal and distal ends 130, 132. For example, a shape of the first member 120 can include or define first, second and third regions 140, 142, 144. The first member 120 has a substantially uniform outer dimension (i.e., within 5 percent of a truly uniform shape) along the first region 140, for example a substantially uniform outer diameter. The first member 120 has a tapering outer dimension (e.g., tapering outer diameter) along the second region 142 (i.e., tapering from the first region 140 to the third region 144), and a substantially uniform outer dimension along the third region 144. With this construction, and outer dimension (e.g., outer diameter) of the first member 120 along the first region 140 is greater than the outer dimension of the first member 120 along the third region 144. As described in greater detail below, in some embodiments a shape or outer dimension of one or both of the first and third regions 140, 144 can be selected in accordance with geometries or dimensions of other components of the balloon catheter 20 (FIG. 1). The first member 120 can have other shapes or profiles that may or may not include the taper reflected by FIG. 5 (e.g., the first member 120 can have a uniform outer dimension (e.g., diameter) in extension between the proximal and distal ends 130, 132; can have multiple variations in shape; etc.). In some embodiments, the first member 120 can be a rigid, solid body (e.g., a metal wire), although other constructions (e.g., a tubular) are also acceptable.

The second member 122 is a rigid body defining opposing, trailing and leading ends 150, 152 and a length L2. The second member 122 is akin to a ring or tube, having an internal passage 154. A size and shape of the internal passage 154 is selected in accordance with geometries of the first member 120 such that the first member 120 can be received within the internal passage 154. For example, in some embodiments, the internal passage 154 is sized and shaped to be received over the first region 140 of the first member 120. Stated otherwise, with embodiments in which the first member 120 incorporates the taper features described above, including the first region 140 defining a maximum outer dimension (e.g., diameter) of the first member 120, a dimension (e.g., diameter) of the internal passage 154 is selected to approximate (e.g., equal to or slightly greater than) the maximum outer dimension of the first member 120. As described below, other geometry relationships between the internal passage 154 and shape or outer dimensions of the first member 120 are also envisioned. In some embodiments, the internal passage 154 has a substantially uniform dimension (e.g., within 5 percent of a truly uniform dimension) in extension between the trailing and leading ends 150, 152, such as a substantially uniform diameter. In related embodiments, an outer dimension (e.g., outer diameter) of the second member 122 can also be substantially uniform in extension between the trailing and leading ends 150, 152. Regardless, the length L2 of the second member 122 is selected to be less than the length L1 of the first member 120, although a relationship between the lengths L1, L2 is in no way limited to that generally reflected by the views.

Figure 6A:
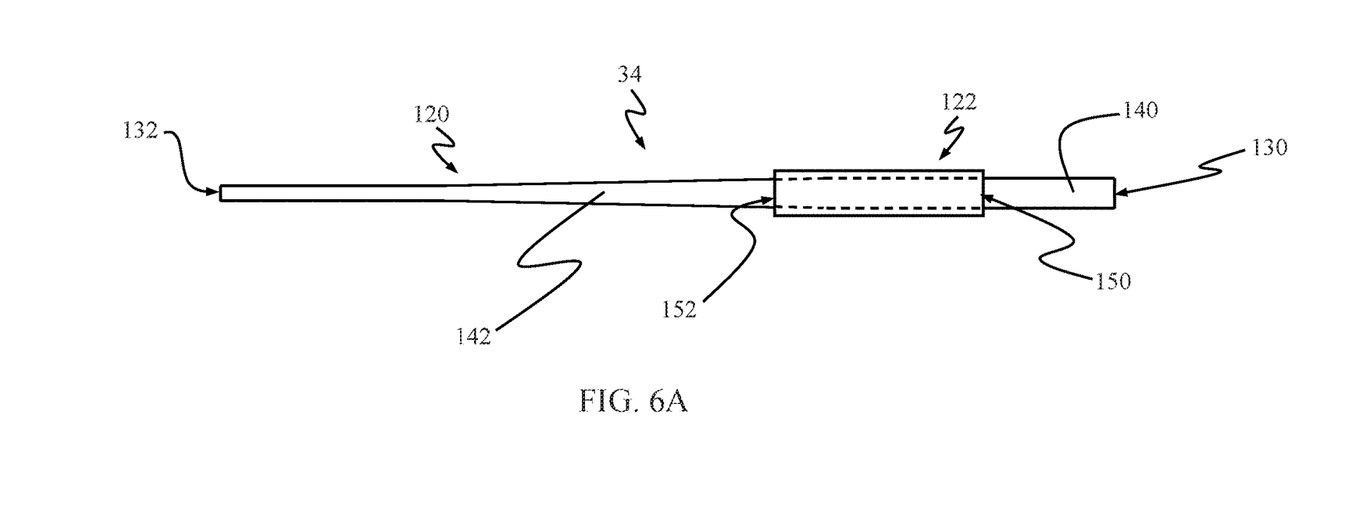
FIG. 6A is a side view of the support assembly of FIG. 5 upon final construction.
Figure 6B:
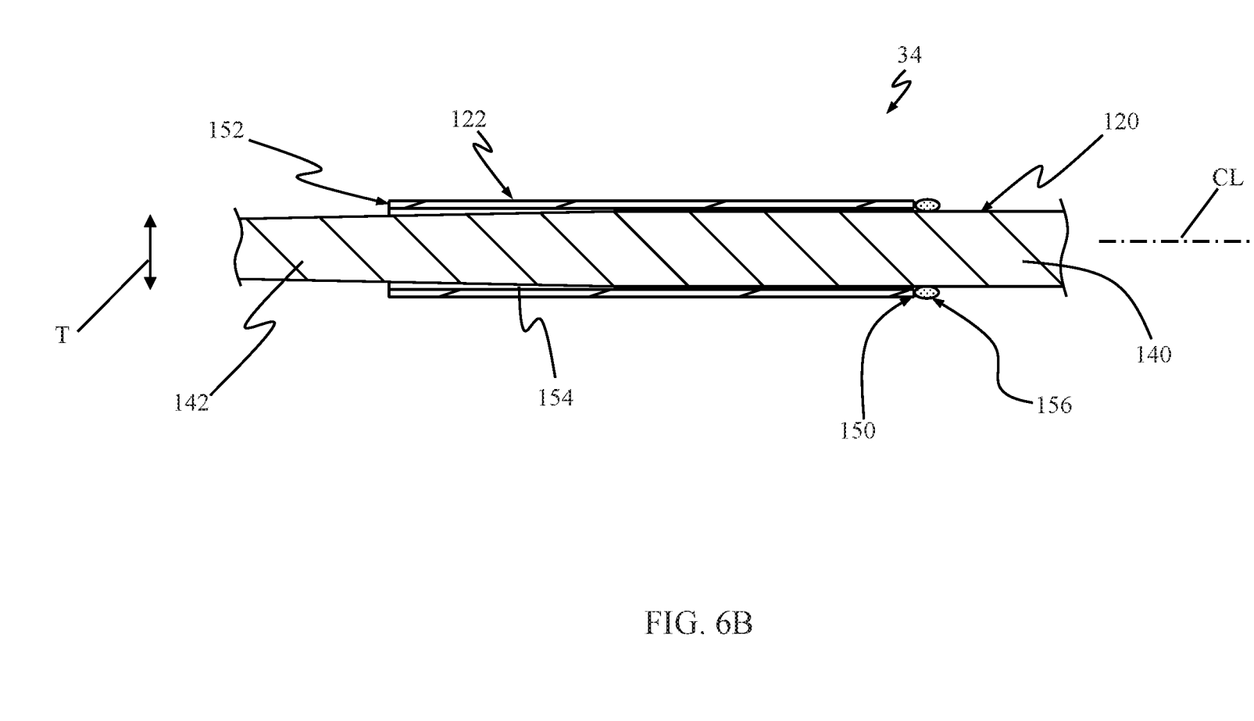
FIG. 6B is an enlarged cross-sectional view of a portion of the support assembly of FIG. 6A.

Placement of the second member 122 over the first member 120 in providing the completed support assembly 34 is shown in FIGS. 6A and 6B. The first member 120 nests within the internal passage 154 of the second member 122. An entirety of the second member 122 can be positioned longitudinally between the proximal and distal ends 130, 132 of the first member 120, with the leading end 152 arranged distal the trailing end 150. In some non-limiting embodiments, the second member 122 can be fixed or directly, physically attached to the first member 120 at or immediately proximate the trailing end 150. For example, the second member 122 can be welded, bonded, adhered, mechanically coupled, etc., to the first member 120 at or immediately proximate the trailing end 150. By way of non-limiting example, FIG. 6B generally reflects this direct, physical attachment as being effectuated by a weld 156 formed at the trailing end 150. In other embodiments, an entirety of the second member 122 is free of direct, physical attachment to the first member 120. Regardless, in some embodiments of the present disclosure, the leading end 152 of the second member is free of direct, physical attachment to the first member 120; alternatively, at least a majority of a length of the second member 122 in extension from (and including) the leading end 152 is free of direct, physical attachment to the first member 120. With these and related embodiments, the leading end 152 can deflect or articulate or move transversely relative to the first member 120 (generally represented by the arrow "T" in FIG. 6B) for reasons made clear below. In related embodiments, an arrangement of the second member 122 relative to the first member 120 can enhance an available range of transverse articulation of the leading end 152, for example akin to the arrangement best seen in FIG. 6B in which the trailing end 150 is located over a maximum outer dimension of the first member 120 (e.g., the first region 140) and a location of the leading end 152 corresponds to a less-than-maximum outer dimension of the first member 120 (e.g., the second region 142). Regardless, and upon final constructions, the support assembly 34 defines a centerline CL, with the leading end 152 generating or serving as a radially or transversely projecting face of the support assembly 34 relative to the centerline CL.

With the above explanations in mind, the first and second member 120, 122 are separately manufactured or provided, and subsequently assembled to one another. In other words, geometries embodied by the support assembly 34 (e.g., the transverse face provided by the leading end 152 of the second member 122 as assembled over the first member 120) are not machined or otherwise formed into a single, homogenous body. The support assembly 34 is thus readily and inexpensively manufactured.

Figure 7:
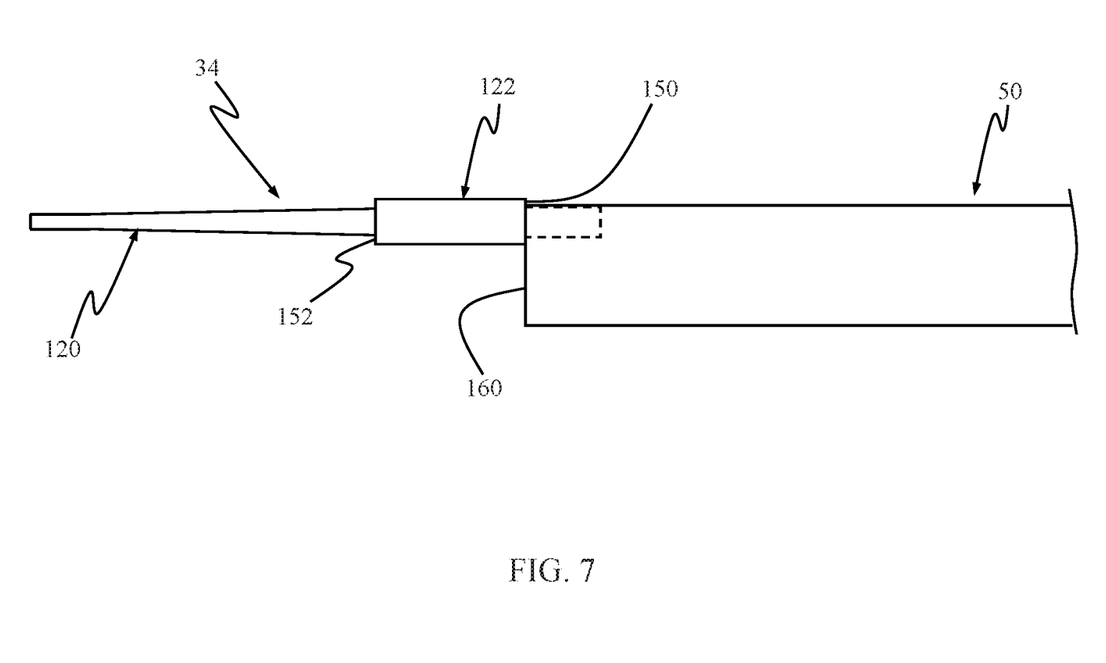
FIG. 7 is a simplified side view illustrating mounting of the support of assembly of FIG. 6A to another component of the balloon catheter of FIG. 1.

Returning to FIG. 1, the support assembly 34 can be mounted to or carried by one or more other components of the balloon catheter 20. In some embodiments, the support assembly 34 can be mounted to the catheter shaft 30, and in particular the proximal shaft segment 50. For example, FIG. 7 illustrates a portion of the proximal shaft segment 50 along with the support assembly 34. The proximal shaft segment 50 terminates at a distal side 160 and, as described above, can be a hypotube or similar structure that forms the lumen 60 (hidden in FIG. 7, but shown, for example, in FIG. 2). Mounting of the support assembly 34 to the proximal shaft segment 50 can include a portion of the first member 120 being located within the lumen 60 and attached (e.g., welded, bonded, adhered, etc.) to an interior surface of the proximal shaft segment 50. A remainder of the first member 120 extends distally beyond the distal side 160 (and is thus exposed relative to the proximal shaft segment 50). The second member 122 is located distal the distal side 160, extending over a portion of the first member 120 as described above. The trialing end 150 can be flush against the distal side 160 as shown; alternatively, a gap can be formed between the second member 122 and the distal side 160. In some embodiments, the first member 120 is initially secured (e.g., welded) to the proximal shaft segment 50, followed by placement of the second member 122 over the first member 120; once placed at a desired location, the second member 122 can be directly, physically secured to the first member 120 as described above (or, alternatively, the second member 122 can be entirely free of direct physical attachment to the first member 120). In other embodiments, the second member 122 is first attached to the first member 120 as described above, followed by attachment of the first member 120 to the proximal shaft segment 50. Other mounting configurations are also envisioned.

Figure 8:
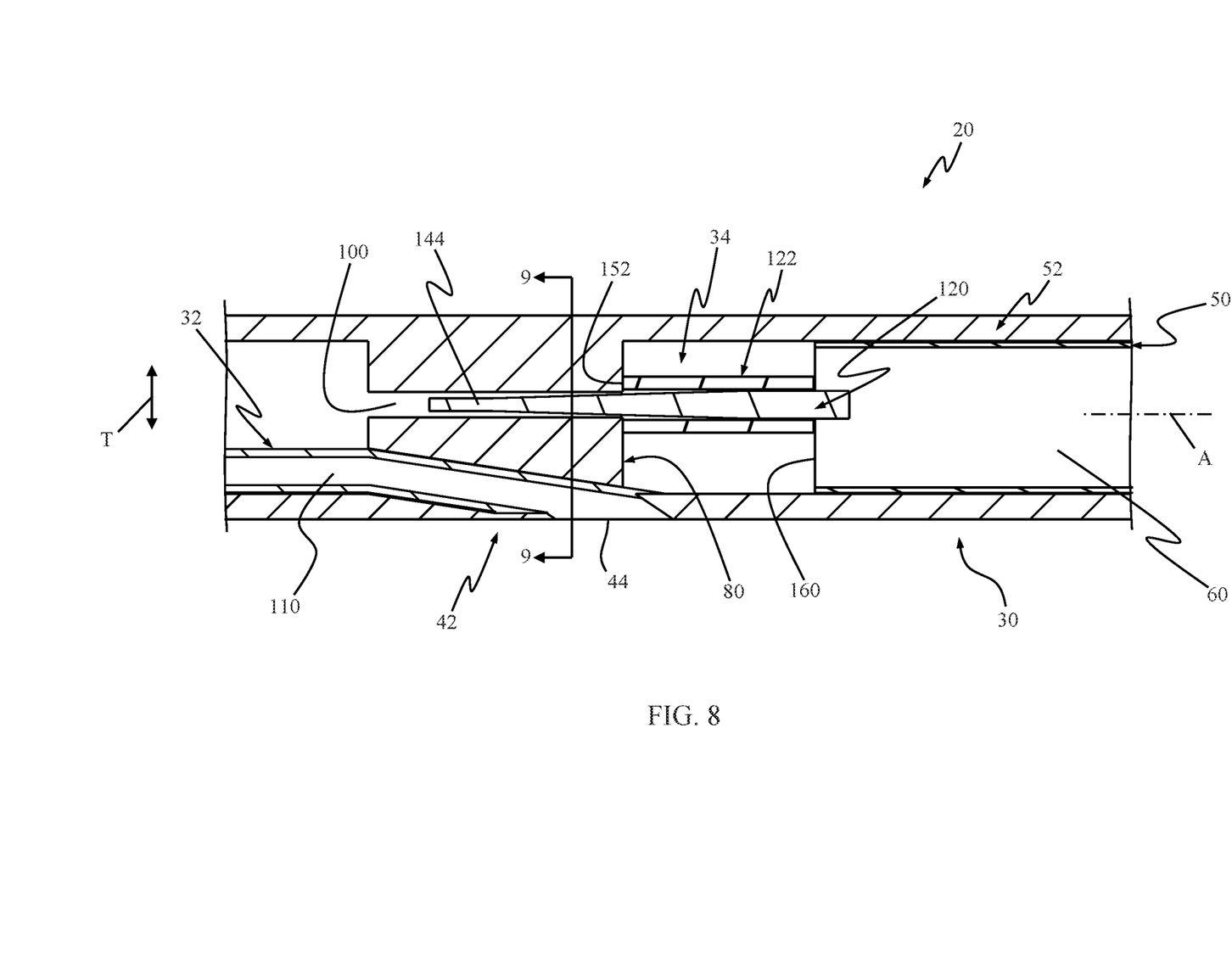
FIG. 8 is an enlarged cross-sectional view of a portion of the balloon catheter of FIG. 1.

Arrangement of the support assembly 34 upon final construction of the balloon catheter 20 is shown in FIG. 8 (that is otherwise a longitudinal cross-section of the balloon catheter 20 at the region R identified in FIG. 1). As described above, the support assembly 34 is mounted to the proximal shaft segment 50, with the second member 122 (and a portion of the first member 120) located distal the distal side 160. A portion of the first member 120 (e.g., the third region 144) is slidably received within the transition lumen 100. FIG. 8 further reflects the leading end 152 of the second member 122 as abutting or bearing against the proximal internal shoulder 80 of the distal shaft segment 52. Geometries of the support assembly 34, the proximal shaft segment 50, and the distal shaft segment 52 can be such that in the absence of external forces (e.g., absence of a pushing force being applied to the proximal shaft segment 50 in the distal direction and/or absence of a resistive force being applied to the distal shaft segment 52 in the proximal direction), the leading end 152 of the second member 122 is in contact with the proximal internal shoulder 80. Alternatively, geometries can be selected such that a longitudinal gap is formed between the leading end 152 and the proximal internal shoulder 80 in the absence of external forces, with the leading end 152 being brought into contact with the proximal internal shoulder 80 in response, for example, to distal movement of the proximal shaft segment 50 relative to the distal shaft segment 52 (e.g., a pushing force applied by a user onto the proximal shaft segment 50). Regardless, with abutting contact between the leading end 152 and the proximal internal shoulder 80, a pushing force applied onto the proximal shaft segment 50 (e.g., a pushing force applied by a user at or near the hub assembly 38 (FIG. 1)) is transferred by the support assembly 34 onto the distal shaft segment 52 in a region of the rapid exchange joint 42 via the proximal internal shoulder 80/leading end 152 interface. Stated otherwise, abutting interface between the proximal internal shoulder 80 and the leading end 152 is along a plane that is substantially perpendicular (i.e., within 10 degrees of a truly perpendicular relationship) to the central longitudinal axis A; a longitudinal force (i.e., a force direction parallel with the central longitudinal axis A) applied to the proximal shaft segment 50 will be perpendicular to the plane of interface and is transferred onto the proximal internal shoulder 80 as a longitudinal force via the leading end 152.

Returning to FIG. 1, the balloon 36 can assume various forms known in the art appropriate for a desired balloon catheter-based procedure. For example, the balloon 36 can be made from a thermoplastic material or a thermoplastic elastomer, such as various polyesters and their block co-polymers, polyamides and their block co-polymers and polyurethane block co-polymers. Some exemplary balloon materials and constructions are described in U.S. Pat. Nos. 5,290,306; 6,171,278; 6,210,346; and U.S. Patent Application Publication No. 2006/0134357, the entire teachings of each of which are incorporated herein by reference.

The hub assembly 38 can also assume various forms known in the art appropriate for a desired balloon catheter-based procedure. For example, the hub assembly 38 can include a hub 180 and an optional strain relief body 182. The hub 180 can be or include a luer fitting for delivering an inflation medium to an inflation lumen of the catheter shaft 30 (e.g., the lumen 60 (FIG. 2) of the proximal shaft segment 50). The strain relief body 182, where provided, can have a flexible construction (i.e., more flexible than a construction of the hub 180) and retains the hub 180 relative to the proximal end 46 of the catheter shaft 30 in a manner providing fluid communication between an interior of the hub 180 and the inflation lumen of the catheter shaft 30. The hub assembly 38 can assume a wide variety of other constructions known in the art that may or may not be directly implicated by the illustration of FIG. 1.

Figure 9:
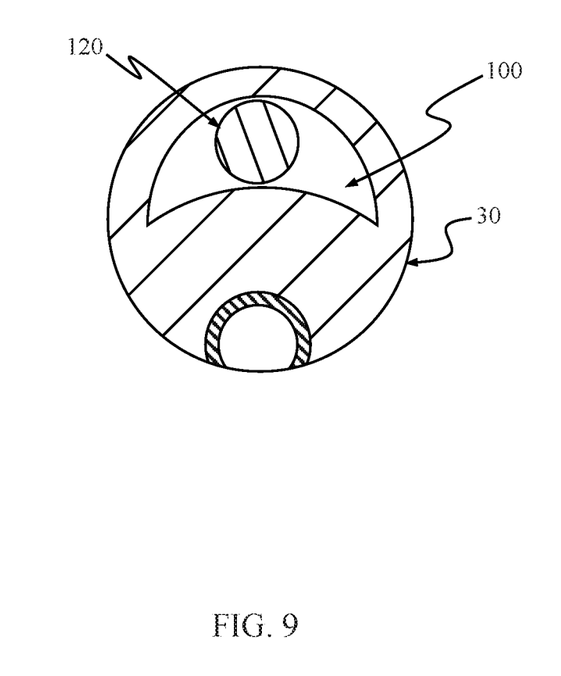
FIG. 9 is a cross-sectional view of the balloon catheter of FIG. 8, taken along the line 9-9.
Figure 10:
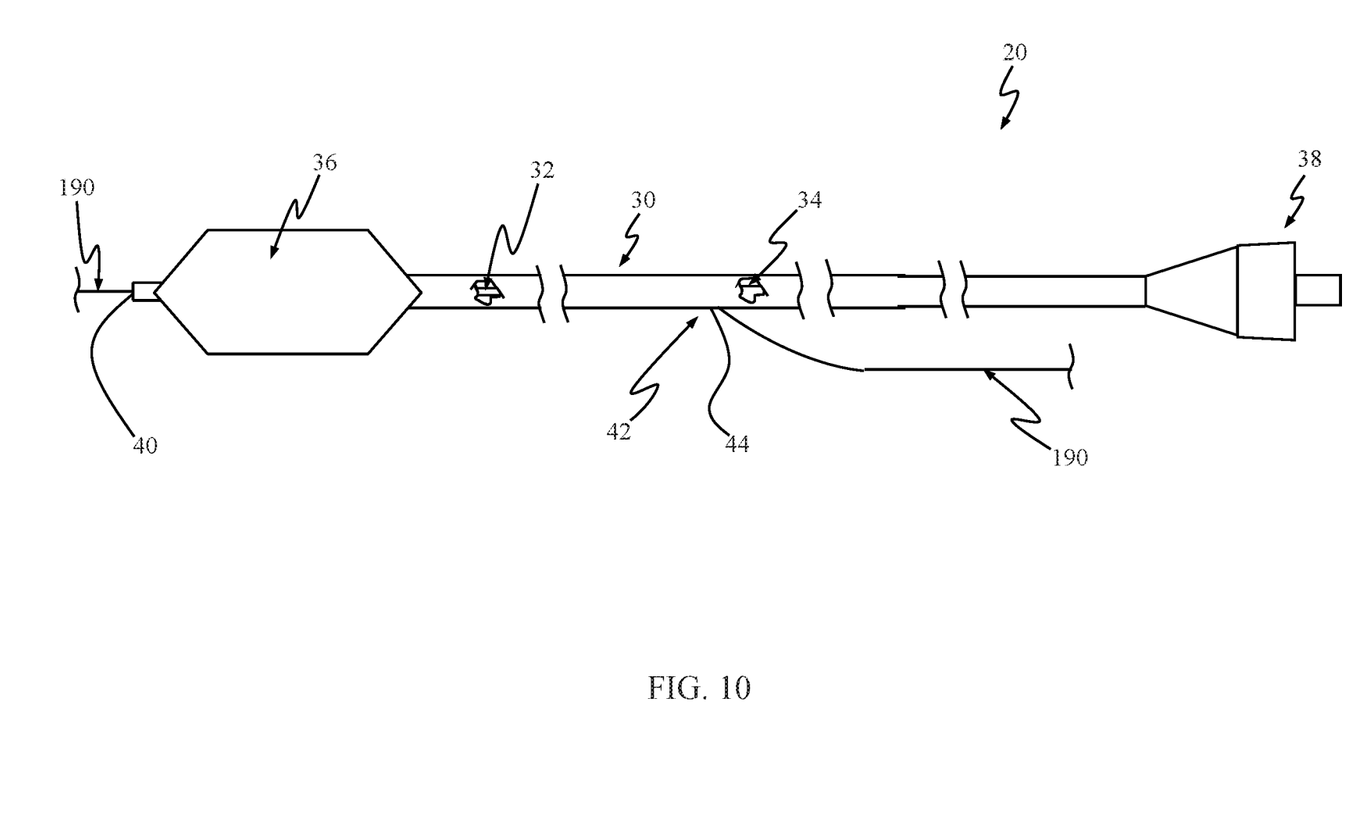
FIG. 10 is a simplified side view of the balloon catheter of FIG. 1 loaded over a guidewire.

With cross-reference between FIGS. 8-10, the balloon catheter 20 can be used for various surgical procedures such as, but not limited to, angioplasty, delivery of a stent or stented medical device, etc. For example, a guidewire 190 can be percutaneously directed to, optionally beyond, a target site within a patient's body (e.g., within the patient's vasculature). The balloon catheter 20 is loaded onto the guidewire 190 (e.g., before or after placement of the guidewire 190 into the patient) via the rapid exchange features as is conventionally known. For example, the guidewire 190 is threaded into the guidewire lumen 110 of the guidewire tube 32 at the distal end 40 of the catheter shaft 30, then through the guidewire lumen 110 and exiting the catheter shaft 30 at the guidewire port 44 of the rapid exchange joint 42. The balloon catheter 20 can then be advanced over the guidewire 190, directing the balloon 36 to the target site. Movement of the balloon catheter 20 through the patient is enhanced by presence of the support assembly 34; a pushing force applied by a user onto the catheter shaft 30 from outside the patient (e.g., at or adjacent the hub assembly 38) is distally transferred, at least partially, by the proximal support assembly 34 onto the catheter shaft 30 in a region of the rapid exchange joint 40 as described above (e.g., the leading end 152 of the second member 122 is in contact with the proximal internal shoulder 80). Moreover, because the leading end 152 can move transversely relative to the first member 120 (arrow "T" in FIG. 8), transverse forces imparted onto the support assembly 34 as the catheter shaft 30 traverses tortuous pathways are lessened (as compared to a construction in which the second member 122 were entirely rigidly fixed to the first member 120), thus minimizing the possibility of kinks being formed in the first member 120. The balloon 36 can be inflated and deflated as desired via an inflation medium supplied, for example, via the hub assembly 38 to the lumen 60 of the proximal shaft segment 50. In some embodiments, and as best shown in FIG. 9, the first member 120 does not occlude the transition lumen 110, allowing the inflation medium to freely flow to the balloon 36. Once the intended procedure (or portion of an overall procedure) using the balloon catheter 20 is complete, the balloon catheter 20 can be removed from the patient over the guidewire 190; optionally, another medical device can then be delivered to the target site over the guidewire 190.

Figure 11:
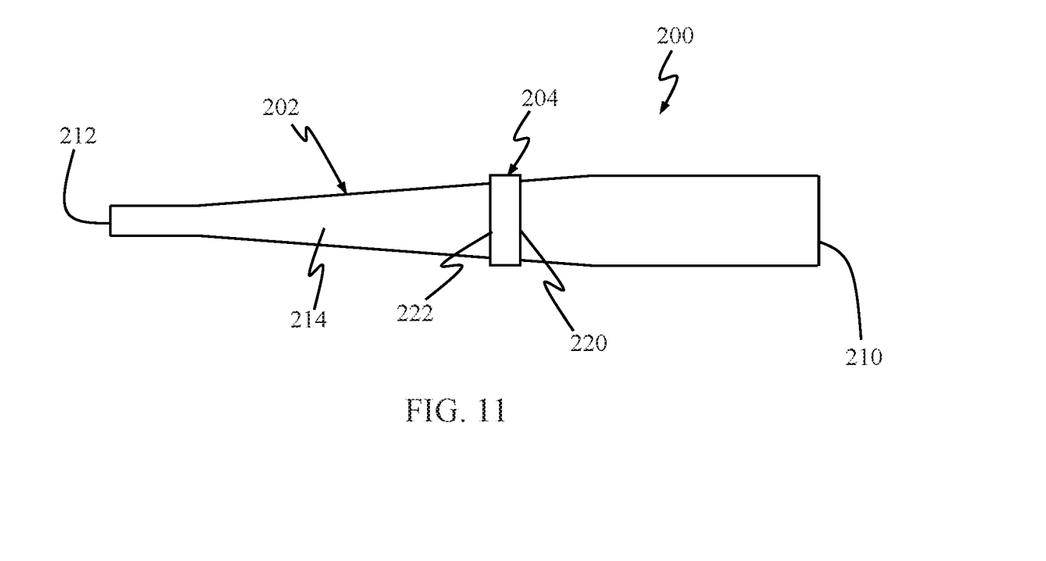
FIG. 11 is a simplified side view of another support assembly in accordance with principles of the present disclosure and useful with the balloon catheter of FIG. 1.

Another support assembly 200 in accordance with principles of the present disclosure, for example with the balloon catheter 20 (FIG. 1) described above, is shown in simplified form in FIG. 11. The support assembly 200 includes a first member 202 and a second member 204. As with previous embodiments, the first and second members 202, 204 are discrete components or bodies that are separately formed or manufactured, and subsequently assembled. The first member 202 can be akin to the first member 120 (FIG. 5) described above, such as a solid body (push rod), and defines opposing, proximal and distal ends 210, 212, and a tapered region 214. The second member 204 can be akin to the second member 122 (FIG. 5) described above, such as a ring or tube, and defines opposing, trailing and leading ends 220, 222, and a lumen (hidden in FIG. 11). A longitudinal length of the second member 204 is less than a longitudinal length of the first member 202, and a diameter of the lumen of the second member 204 is selected to "fit" over the tapered region 214. In the mounted state of FIG. 11, the trailing end 220 of the second member 204 is secured to the first member 202 (e.g., press-fit, weld, adhesive, bond, etc.), whereas the leading end 222 is free of direct physical attachment to the first member 202. Thus, the leading end 222 can move transversely relative to the first member 202 in accord with the descriptions above.

The support assembly 200 can be utilized as part of a balloon catheter in various manners. For example, and with additional reference to FIG. 8, the support assembly 200 can be used in place of the support assembly 34, with the first member 202 mounted to the proximal shaft segment 50 and the second member 204 positioned such that the leading end 222 interfaces with the proximal internal shoulder 80.

Figure 12:
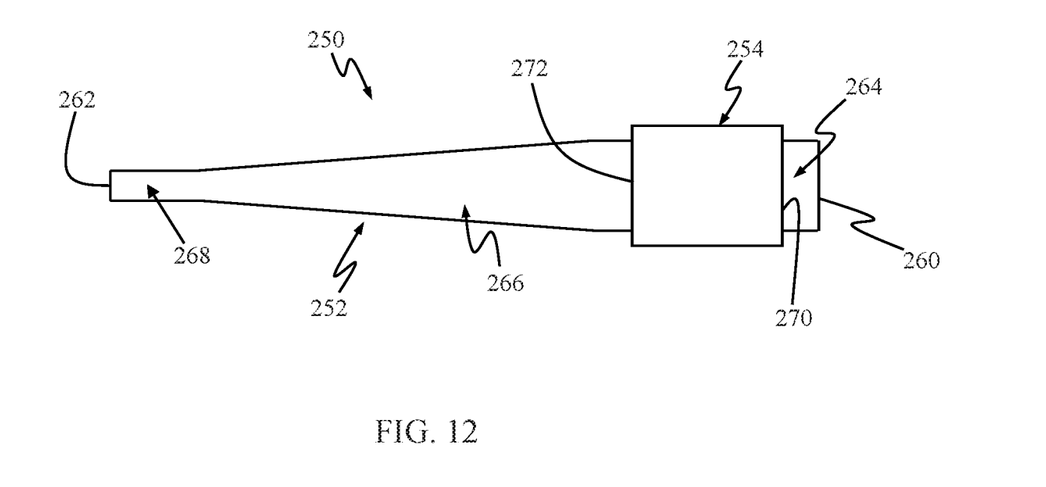
FIG. 12 is a simplified side view of another support assembly in accordance with principles of the present disclosure and useful with the balloon catheter of FIG. 1.

Another support assembly 250 in accordance with principles of the present disclosure, for example with the balloon catheter 20 (FIG. 1) described above, is shown in simplified form in FIG. 12. The support assembly 250 includes a first member 252 and a second member 254. As with previous embodiments, the first and second members 252, 254 are discrete components or bodies that are separately formed or manufactured, and subsequently assembled. The first member 252 can be akin to the first member 120 (FIG. 5) described above, such as a solid body (push rod), and defines opposing, proximal and distal ends 260, 262, a proximal region 264, a tapered region 266, and a distal region 268. The second member 254 can be akin to the second member 122 (FIG. 5) described above, such as a ring or tube, and defines opposing, trailing and leading ends 270, 272, and a lumen (hidden in FIG. 12). A longitudinal length of the second member 254 is less than a longitudinal length of the first member 252, and a diameter of the lumen of the second member 254 is selected to "fit" over the proximal region 264. In the mounted state of FIG. 12, the trailing end 270 of the second member 254 can be directly physically secured to the first member 252 (e.g., press-fit, weld, adhesive, bond, etc.), or can be free of direct physical attachment to the first member 252. Regardless, the leading end 272 is free of direct physical attachment to the first member 252. Thus, the leading end 272 can move transversely relative to the first member 252 in accord with the descriptions above.

The support assembly 250 can be utilized as part of a balloon catheter in various manners. For example, and with additional reference to FIG. 8, the support assembly 250 can be used in place of the support assembly 34, with the first member 252 mounted to the proximal shaft segment 50 and the second member 254 positioned such that the leading end 272 interfaces with the proximal internal shoulder 80.

The rapid exchange balloon catheters of the present disclosure provide a marked improvement over previous designs. The support assemblies of the present disclosure facilitate desired pushing force transfer from a proximal region of the catheter shaft to other regions distal the proximal region, such as at or proximate a rapid exchange joint. By forming the support assembly from two discrete components, the support assemblies of the present disclosure can be simply and inexpensively manufactured. Further, with the balloon catheters of the present disclosure, the support assembly is less likely to experience kinking as the balloon catheter traverses a tortuous pathway (as compared to conventional rapid exchange balloon catheter/support assembly designs).

Although the present disclosure has been described with reference to preferred embodiments, workers skilled in the art will recognize that changes can be made in form and detail without departing from the spirit and scope of the present disclosure.

What is claimed is:

1. A balloon catheter comprising:
 a catheter shaft defining a plurality of lumens and an internal shoulder;
 a balloon carried by the catheter shaft, wherein an interior of the balloon is fluidly open to at least one of the plurality of lumens; and
 a support assembly comprising:
  a first member extending between opposing, proximal and distal ends,
  a second member disposed over the first member, the second member defining opposing, leading and trailing ends, wherein the second member is arranged such that the leading end is distal the trailing end, wherein the leading end of the second member is free of direct physical attachment to the first member;
 wherein the support assembly extends within one of the plurality of lumens and the leading end of the second member bears against the internal shoulder.

2. The balloon catheter of claim 1, wherein the trailing end of the second member is directly attached to the first member.

3. The balloon catheter of claim 1, wherein the first member is a solid body and the second member is a tube.

4. The balloon catheter of claim 1, wherein the first member defines a first region having a uniform outer diameter and a second region having a distally tapering outer diameter, and further wherein the trailing end of the second member is directly attached to the first region.

5. The balloon catheter of claim 1, wherein the first member defines a first region having a uniform outer diameter and a second region having a distally tapering outer diameter, and further wherein the trailing end of the second member is directly attached to the second region.

6. The balloon catheter of claim 1, wherein the catheter shaft includes a proximal shaft segment and a distal shaft segment, and further wherein the first member is attached to the proximal shaft segment.

7. The balloon catheter of claim 6, wherein a maximum outer diameter of the first member is less than a maximum outer diameter of the proximal shaft segment.

8. The balloon catheter of claim 7, wherein a maximum outer diameter of the second member is less than the maximum outer diameter of the proximal shaft segment.

9. The balloon catheter of claim 6, wherein the proximal shaft segment includes a hypotube, and further wherein the first member is directly attached to an interior surface of the hypotube.

10. The balloon catheter of claim 6, wherein the balloon is carried by the distal shaft segment, and further wherein the distal shaft segment includes an outer tube attached to and extending distally from the proximal shaft segment.

11. The balloon catheter of claim 10, wherein the outer tube defines a guidewire port, and further wherein the balloon catheter further comprises a guidewire tube in fluid communication with the guidewire port, and even further wherein the internal shoulder is proximate the guidewire port.

12. The balloon catheter of claim 1, wherein the leading end of the second member is transversely moveable relative to the first member.

13. The balloon catheter of claim 1, further comprising a hub assembly attached to a proximal region of the catheter shaft, wherein the hub assembly defines an inflation passage way in fluid communication with at least one of the plurality of lumens.

14. The balloon catheter of claim 1, wherein the catheter shaft defines a catheter shaft distal end opposite a catheter shaft proximal end, and further wherein the balloon is located adjacent the catheter shaft distal end, and even further wherein the trailing end of the second member is spaced from the leading end of the second member in a direction of the catheter shaft proximal end.

15. A method of performing a surgical procedure on a patient, the method comprising:
 directing a guidewire to a target site within the patient;
 advancing a balloon catheter over the guidewire and into the patient, the balloon catheter including:
  a catheter shaft defining a plurality of lumens and an internal shoulder,
  a balloon carried by the catheter shaft, wherein an interior of the balloon is fluidly open to at least one of the plurality of lumens, and
  a support assembly comprising:
   a first member extending between opposing, proximal and distal ends,
   a second member disposed over the first member, the second member defining opposing, leading and trailing ends, wherein the second member is arranged such that the leading end is distal the trailing end,
   wherein the leading end of the second member is free of direct physical attachment to the first member;
  wherein the support assembly extends within one of the plurality of lumens and the leading end of the second member bears against the internal shoulder;
 wherein the step of advancing a balloon catheter includes the support assembly transferring a pushing force applied to a proximal region of the catheter shaft onto a region of the catheter shaft distal the proximal region;
 inflating the balloon;
 deflating the balloon; and
 withdrawing the balloon catheter from the patient.

16. The method of claim 15, wherein the step of advancing a balloon catheter includes the leading end of the second member moving transversely relative to the first member.

17. The method of claim 15, wherein the surgical procedure is an angioplasty procedure.

18. The method of claim 15, wherein the surgical procedure is a stent delivery procedure.

* * * * *